(12) United States Patent
Belalcazar et al.

(10) Patent No.: US 8,190,246 B2
(45) Date of Patent: May 29, 2012

(54) SENSING BIOLOGICAL DATA (75) Inventors: Andres Belalcazar, St. Paul, MN (US);
Jack D. Stewart, Plymouth, MN (US);
Ji Chen, Woodbury, MN (US)

(73) Assignee: Greatbatch Ltd., Clarence, NY (US)

( * ) Notice: Subject to any disclaimer, the term of this patent is extended or adjusted under 35 U.S.C. 154(b) by 487 days.

(21) Appl. No.: 12/163,596

(22) Filed: Jun. 27, 2008

(65) Prior Publication Data
US 2009/0326398 A1    Dec. 31, 2009

(51) Int. Cl.
*A61B 5/04* (2006.01)
(52) U.S. Cl. ........................................... 600/509
(58) Field of Classification Search .................. 600/509; 607/2–3, 36
See application file for complete search history.

(56) References Cited

U.S. PATENT DOCUMENTS

| | | | |
|---|---|---|---|
| 5,518,001 A | 5/1996 | Snell | |
| 5,987,352 A | 11/1999 | Klein et al. | |
| 6,738,671 B2 * | 5/2004 | Christophersom et al. | 607/60 |
| 7,912,537 B2 * | 3/2011 | Lee et al. | 600/547 |
| 2002/0019586 A1 * | 2/2002 | Teller et al. | 600/300 |
| 2005/0103351 A1 * | 5/2005 | Stomberg et al. | 128/898 |
| 2006/0235489 A1 | 10/2006 | Drew et al. | |
| 2007/0016089 A1 | 1/2007 | Fischell et al. | |
| 2007/0123786 A1 | 5/2007 | Grandjean et al. | |
| 2007/0208263 A1 | 9/2007 | John et al. | |
| 2008/0058664 A1 * | 3/2008 | Mirro | 600/523 |

* cited by examiner

*Primary Examiner* — Carl H Layno
*Assistant Examiner* — Paula J Stice
(74) *Attorney, Agent, or Firm* — Michael F. Scalise; Fish & Richardson P.C.

(57) ABSTRACT

A system is provided for obtaining and analyzing biological data of a subject. The system includes a biological data recording device that can sense biological signals of a subject over time and record the sensed biological signals as biological data. The system also includes an event time recording device that is physically separate from, and does not communicate with, the biological data recording device. The event time recording device includes a user actuatable component, and also includes a recording component that records user actuation data, which includes a time stamp indication as to when any instances of user actuation occurred. The system also includes equipment that can periodically receive the recorded biological data from the biological data recording device and the user actuation data from the event time recording device, and can correlate the biological data and the user actuation data to generate correlated biological data.

20 Claims, 6 Drawing Sheets

FIG. 6A
(Base Station Correlation)

FIG. 6B
(Secure Site Correlation)

SENSING BIOLOGICAL DATA

TECHNICAL FIELD

This disclosure relates to sensing and recording biological data in a subject, and correlating the recorded biological data to symptomatic events felt by the subject.

BACKGROUND

Implantable medical devices are used in patients in order to diagnose root causes for various symptomatic events. For example, implantable loop recorders (ILRs) are used in patients with syncope, or fainting. Traditionally, these implantable devices are used in conjunction with an activator, which the patient or family can use to command the implanted device to store a rhythm in the ILR's memory at the moment of a symptomatic event. However, activators are relatively large devices, which the patient must carry at all times.

Some implantable medical devices include automatic recording of sensed physiological data upon some triggering mechanism, which may be based upon a sensed physiological condition of the patient. However, these automatic recording devices may produce many strips in addition to the strips associated with a symptomatic event, thus making the analysis of the recorded rhythms onerous and inefficient.

SUMMARY

In one general aspect, a system is provided for obtaining and analyzing biological data of a subject. The system includes a biological data recording device that can sense biological signals of a subject over time and record the sensed biological signals as biological data. The system also includes an event time recording device that is physically separate from, and not adapted to communicate with, the biological data recording device. The event time recording device includes a user actuatable component that can be actuated by a user, and also includes a recording component that records user actuation data, which includes a time stamp indication as to when any instances of user actuation occurred. The system also includes equipment that can periodically receive the recorded biological data from the biological data recording device and the user actuation data from the event time recording device, and can correlate the biological data and the user actuation data to generate correlated biological data.

In various implementations, the biological data recording device may be an electrocardiogram (ECG) recording device. The biological data recording device may be implantable and have a wireless transmitter to transmit recorded biological data, and the equipment may have a wireless receiver to receive the recorded biological data transmitted by the implantable ECG recording device. The event time recording device may be a timekeeping device, such as a watch, or may be a keychain. The event time recording device may have a wireless transmitter to transmit user actuation data, and the equipment may have a wireless receiver to receive the user actuation data transmitted by the event time recording device. The equipment may be configured to correct timing information in either the recorded biological data or user actuation data. The event time recording device may periodically transmit one or more periods of recorded user actuation data corresponding to user actuation data recorded during the current time period and during each of a number of previous time periods.

In another general aspect, a method is provided for obtaining and analyzing biological data of a subject. The method includes receiving sensed biological data from a biological data recording device that can sense biological signals of the subject over time and record the sensed biological signals as biological data. The method also includes receiving user actuation data from an event time recording device that is physically separate from the biological data recording device. The event time recording device has a user actuatable component that may be actuated by a user, and a recording component that records user actuation data, including when any instances of user actuation occurred. The method further includes generating correlated biological data by correlating the received sensed biological data and the received user actuation data.

The details of one or more implementations are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1A:
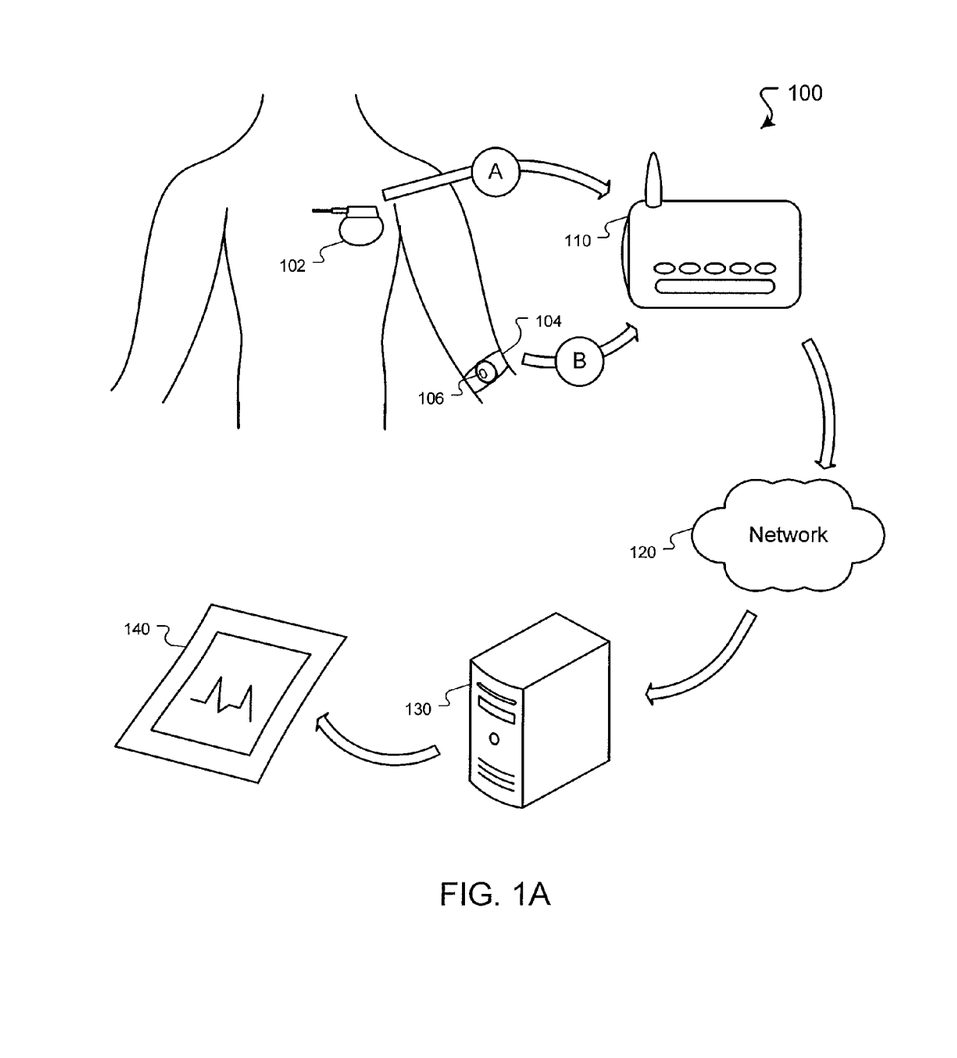
FIG. 1A is a conceptual diagram of a biological sensing system.

FIG. 1A shows an example of a distributed system 100 for sensing and recording biological data in a subject, and for further correlating the sensed biological data with symptomatic events felt by the subject. The system 100 includes a biological data recording device 102 and an event time recording device 104, both of which may be in periodic or constant communication with a base station 110. The base station 110, in turn, may be in periodic or constant communication over a network 120 with a secure remote data center 130. In general, the system 100 may be used to generate a report 140 that may show a physician, for example, sensed biological data that occurred during or near the time of a symptomatic event.

The system 100 may be configured to include an implantable loop recorder (ILR) as the biological data recording device 102 implanted, for example, in a subject with syncope. Other configurations are also within the scope of this disclosure, some of which are discussed below. Syncope, which is commonly referred to as fainting, is characterized by a sudden and temporary loss of consciousness that may occur when the subject's blood pressure is too low, and when the heart does not pump a normal supply of blood and oxygen to the brain. In some implementations, an ILR may be used to evaluate various other conditions such as seizures, drug-refractory epilepsy, recurring heart palpitations, or others.

The biological data recording device 102 may sense and record several sets of biological signals over the course of a given time period—e.g., a minute, an hour, a day, a few days, a week, or more. Depending upon the length of the time period and the recording frequency, many of the recorded signals may not be particularly relevant to diagnosing or analyzing the subject's symptoms or base condition. For example, a data recording device 102 may record thirty different sets of data during a single day, but perhaps only one or two of those recorded events actually correspond with a symptomatic event in the subject. It may thus be inefficient to analyze all of the biological data recorded by the data recording device 102.

Figure 1B:
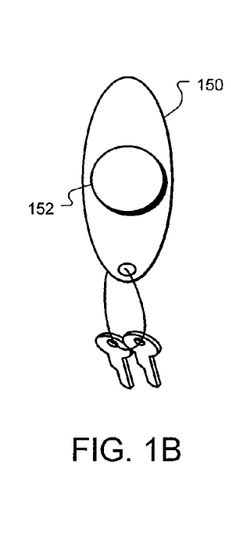
FIG. 1B is an implementation of an event time recording device.

To that end, the subject may wear or carry an event time recording device 104, which can be actuated to record the time when a particular symptomatic event is felt by the subject. In many instances, the subject will be able to feel an oncoming fainting episode prior to fainting actually occurring. Upon feeling the onset of symptoms, the subject or a third party may trigger the device 104 by, for example, pushing a button 106 on the device 104. An alternative implementation of the event time recording device 104 shown in FIG. 1A is shown in FIG. 1B, where the event time recording device 150 is in the form of a keychain 150 with a button 152 for actuation. Triggering of the device 104 may also occur via any other user input, such as by voice activation or the like. In some implementations, triggering of the event time recording device 104 may occur automatically, such as when a gyroscope detects that the subject has rapidly accelerated and then stops moving for a period of time—thus potentially indicating a fainting episode. The event time recording device 104 might also include some application software to help prevent against inadvertent actuations, such as in the automatic triggering example above when, for instance, the subject drops his keys, but then picks them up a short time later. Upon triggering, the event time recording device 104 may store the instance of the symptomatic episode as a time stamp record in its internal memory.

In certain implementations, the event time recording device 104 may have some dual functionality or be of some other use to the subject. For example, the device may be integrated with a wristwatch 104, as shown in FIG. 1A, or may be integrated with a keychain 150, as shown in FIG. 1B. As another example, the device may be integrated with a belt holster that may typically hold a cell phone or a PDA. Other implementations may include a fashion-focused dual functionality, such as where the time recording device 104 is integrated with a ring, a broach, a bracelet, or the like. In some implementations, the event time recording device 104 may include more than one button, each of which may be used to indicate different types of events for the subject. For example, one button may indicate that the subject is feeling cardiac symptoms, while another button may indicate that the subject has just completed eating. Later, when the correlated biological data corresponding to these different indications is analyzed, the data corresponding to a symptomatic event may be analyzed or processed differently than data corresponding to the meal time of the subject. The event time recording device 104 may include any number of different actuation mechanisms, each of which may correspond to one or more subject indications. Some implementations of the event time recording device 104 may include an emergency response dual functionality, such as where the event time recording device 104 is integrated with an emergency help transmitter. In these and other implementations, the subject is not overburdened by carrying any additional bulky medical equipment around during the course of the day, thereby increasing the likelihood of the subject's acceptance and use of the system.

In the system 100 as described above, the biological data recording device 102 does not need to have any communication with the event time recording device 104. Instead, the two devices may record separate information about the symptomatic event—the biological data recording device 102 recording biological data from various measurements occurring before, during, or after the symptomatic event, and the event time recording device 104 recording the timing of the symptomatic event, as indicated by the user. The separation of the two devices allows both the biological data recording device 102 and the event time recording device 104 to have relatively simpler circuitry and to be relatively smaller in size, which in turn may also result in increased patient compliance. Also, according to this implementation, the biological data recording device 102 can devote most or all of its memory to sensing and recording triggered automatic events, thus resulting in a larger capacity for stored biological data.

The biological data may be stored in the internal memory of the biological data recording device 102 and the user actuation data may be stored in the internal memory of the event time recording device 104 until a later time. The stored data from either or of the devices may then be wirelessly transmitted to a separate analytical or intermediate device such as a base station 110 that may be located in the subject's home. This is shown as an example in FIG. 1A, where the recorded biological data is wirelessly transmitted to the base station 110 as shown by arrow A, and the recorded timing data is separately, and also wirelessly, transmitted to the base station 110 as shown by arrow B. The recorded data may also be transferred via a wired connection or any other known data transfer mechanism. Also shown as an example in FIG. 1A, the base station 110 may further be communicably linked via a network 120 to a secure remote data center 130 that may be monitored by health care professionals. In other implementations, the biological recording device 102 and the event time recording device 104 may transmit the sensed biological data and the user actuation data, respectively, directly to the remote data center 130.

Because the biological data recording device 102 and the event time recording device 104 do not have any communication with one another, the base station 110 and/or the remote data center 130 may be configured to correlate the timing of the symptomatic events as recorded by the event time recording device 104 with the corresponding biological data as recorded by the data recording device 102, thus resulting in correlated biological data. In so doing, the biological data that was recorded during a symptomatic event (i.e., the correlated biological data) may be more effectively analyzed.

For instance, a physician, or any other health care provider analyzing the biological data of the subject, may choose to analyze only the data that corresponds with a symptomatic event, and may ask the system 100 to provide a report 140 showing only such correlated biological data. Or, the physician may choose to analyze the entirety of the data, but with more particular focus upon the symptomatic events. In that particular implementation, a report 140 may be generated with some sort of highlighting of the symptomatic events. Alternatively, the physician may ask for a report 140 comparing the biological data recorded during a non-symptomatic event with the biological data of a symptomatic event to evaluate certain trends or patterns.

Figure 2:
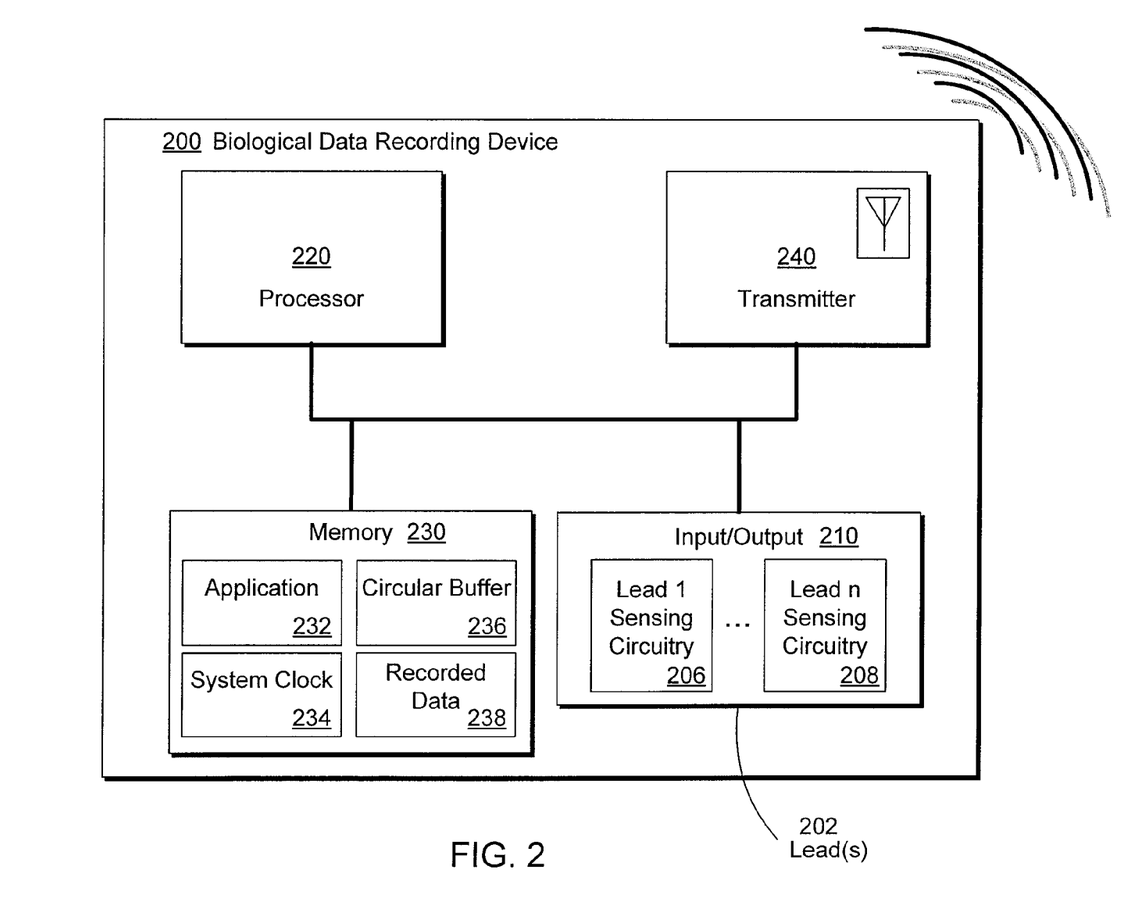
FIG. 2 is a block diagram of a biological data recording device.

FIG. 2 shows an example block diagram of a biological data recording device 200. In some implementations, the device 200 may be configured to sense one or more biological signals in a subject, store the one or more biological signals in memory, and wirelessly transmit the one or more signals or a portion of the signals to an external device for further processing.

In certain implementations, the biological data recording device 200 is a medical device or a portion of a medical device that is subcutaneously implanted in the thoracic region of the subject. As shown as an example in FIG. 1A, the biological data recording device is implanted in the left thoracic region of the subject. But the data recording device 200 may also be implanted in any other part of the subject's body, such as in the abdominal region for example. In some implementations, the data recording device may not be implanted at all, but rather may be used externally, such as a device that is attached to the subject's skin or used in some other manner external to the subject. In other implementations, a combination of more than one data recording device may be used.

The depicted biological recording device 200 includes one or more leads 202, an input/output module 210, including lead sensing circuitry 206, 208 for each of the leads 202, a memory 230, with a number of modules 232, 234, 236, 238, a processor 220, and a transmitter 240. Although the different modules housed within the recording device 200 are shown separately for clarity, in certain implementations, all of the separate modules may be combined into a single application specific integrated circuit (ASIC), without the need for a separate input/output 210, processor 220, memory 230, and transmitter 240. Other implementations are discussed further below.

The biological data recording device 200 shown in FIG. 2 includes one or more leads 202 operably connected to input/output circuitry 210 housed in the device. The one or more leads 202 can include one or more electrodes or sensors that can sense signal data, including biological signal data of the subject. In some implementations, the one or more leads 202 are intracardiac leads. In some implementations, the one or more leads 202 are configured for subcutaneous location within a subject. In some implementations, at least one intracardiac lead and at least one subcutaneous lead are included. In some implementations, the one or more leads 202 depicted in FIG. 2 may include, be replaced by, or be supplemented with one or more sensors, such as blood pressure sensors, or ports configured to sense a biological signal. Some implementations may include one or more catheters that may facilitate mechanical measurements at a distance from the device.

The biological signals measured and recorded by the data recording device 200 can include electrical signals, pressure signals, hemodynamic signals, or any other type of biological signals, and may be sensed using implanted electrodes or sensors, or alternatively, using external electrodes or sensors as described above. Furthermore, any appropriate number of electrodes or sensors may be used, for example one, two, three, four, or more may be used. Corresponding to these one, two, three, four, or more electrodes or sensors may be separate lead sensing circuits, depicted as modules 206, 208 housed in the data recording device 200. In some implementations, a combinations of internal and external electrodes or sensors, or some combination thereof may be used to sense the biological signals.

The biological data recording device 200 is generally configured to sense and record one or more biological signals of the subject. Examples of such biological signals can include an electrocardiogram (ECG) signal, an electrogram (EGM) signal, a blood pressure signal, a blood flow signal, or a signal comprised of impedance measurements. The signal may be measured at various locations within or outside the body, including within a heart chamber (e.g., left ventricle, right ventricle, left atrium, or right atrium), within a body vessel (e.g., within an artery or vein), within or across an organ, at an external location on the subject's skin, and other locations.

In various implementations, the biological signal may be sensed and recorded at multiple periods of time, and each recording may include information corresponding to one or more cycles of the biological signal. As an example, if the biological signal being recorded is a heart beat, and the measurement was recorded over a period of one minute, the recording may include around 70 cycles or beats of the heart.

Upon sensing the biological signals in the subject, the data recording device 200 can store all or a portion of the signal data in internal memory 230. In some implementations, the device 200 may actively sense biological data continuously but may not record the data unless some triggering event occurs. Examples of such a triggering event may include a sustained above-normal heart rate, a sudden increase in blood pressure, or a rapid decrease in blood pressure. In other implementations, the device 200 may record constantly (i.e., full disclosure) or on a particular schedule.

An application 232 running on a processor 220 may be included in certain implementations to control recording procedures in the biological data recording device 200. As an example, the application 232 can use the sensed biological signal data to determine the heart rate of the subject. In turn, the subject's heart rate may be used to analyze the cardiac state of the subject, which may influence whether the biological data recording device 200 will record various biological signals over a period of time.

In the above example, the processor 220 of the data recording device 200 may run an application 232 from internal memory 230 to determine whether the subject has a sustained above-normal heart rate, a sudden increase in blood pressure, or a rapid decrease in blood pressure. If a sustained above-normal heart rate is detected, for example, the application 232 may record and store into recorded data 238 one or more of the biological signals measured before, during, and after the occurrence of the triggering event. The internal memory 230 of the biological data recording device 200 may include a circular buffer 236 for this purpose. The circular buffer 236 may continuously store biological signal data regardless of whether a triggering event has occurred. The circular buffer 236 may contain only short-term storage of the biological data and may be written over as the buffer 236 fills. However, in the case of a triggering event, the entire circular buffer 236 may be captured in the longer-term recorded data store 238 so that the recording device can capture biological signal data that occurred, even prior to any triggering event. The internal memory 230 may also include a system clock 234 that may be accessed by the application 232 to append timing data to the recorded biological signal data in the recorded data store 238.

Following capture of the sensed biological data, the recorded data 238 may be provided to the transmitter 240. In some implementations, the transmitter 240 can send the stored biological data to an external device, such as a remote data center 130 or to some other monitoring device. In other implementations, the transmitter 240 can send the biological signal data wirelessly to an intermediate external device such as a base station 110, which may then transmit all or a portion of the biological signal data over a network 120 to the remote data center 130. Communications between the biological data recording device 200 and the remote data center 130 or base station 110 may be bidirectional or unidirectional, according to various implementations.

The transmission of the recorded data 238 by the transmitter 240 may be scheduled to occur at a particular time, such as at 3:00 am every morning, or at some other time when the subject will likely be near the base station 110. In this implementation, the transmitter may make repeated attempts to send the data to ensure reception by the base station 110.

In some implementations, the transmitter 240 may be configured as a transceiver configured to receive command signals, programming signals, or clock synchronization signals from an external device, such as the base station 110 or a device programmer. For example, the transceiver can receive a command or programming signal indicating that the implanted device 200 should record and transmit a segment of the biological signal data on a specified periodic basis, such as hourly, daily, weekly, or the like. In another example, the transceiver may attempt transmission of the recorded data 238 at a particular time of day, as described above, and repeat the transmission until the transceiver 240 receives a signal back from the base station 110 that it has received the transmitted biological signal data. In certain implementations, upon receiving the "data received" signal back from the base station 110, the device 200 may clear the recorded data 238 from the memory 230. In another example, the transceiver may periodically attempt transmission of the recorded data 238, and repeat the transmission until the transceiver 240 receives a signal back from the base station 110 that it has received the transmitted biological signal data. In another example, instead of automatically sending the biological signal data to the base station 110 at a particular time every day, the data recording device 200 may be configured to receive interrogation signals from the base station 110, and upon receiving such an interrogation signal, the biological signal data may be sent from the transmitter 240. In another example, the transceiver may receive current clock information from an external source such as the base station 110 or a time-keeping radio station or satellite. In this particular implementation, a clock synchronization subroutine may correct the system clock 234 with the proper time on a periodic basis.

Figure 3:
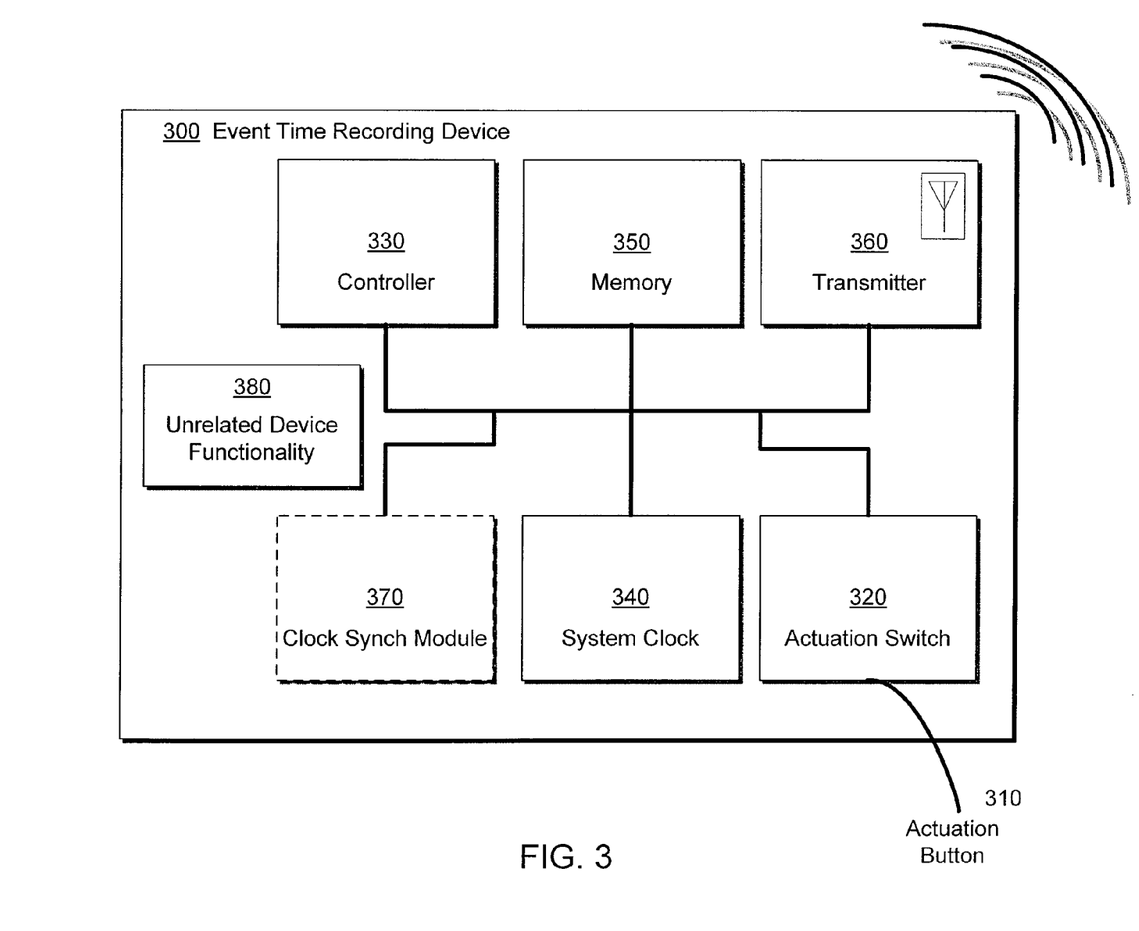
FIG. 3 is a block diagram of an event time recording device.

FIG. 3 shows an example block diagram of an event time recording device 300. In some implementations, the event time recording device 300 may be configured to record and store timing data from one or more occurrences of user actuation at the time of a symptomatic event and to wirelessly transmit the timing data to an external device for further processing. As described above with respect to the biological data recording device 200, the event time recording device 300 is shown in FIG. 3 as separate components only for clarity purposes. The actuation switch 320, controller 330, system clock 340, memory 350, transmitter 360, and optional clock synchronization module 370 may all be integrated into a single ASIC for sizing and power consumption purposes.

As discussed above, the event time recording device 300 may be integrated into any one of a number of items that a subject may typically wear or carry on a daily basis, such as a wristwatch, a keychain, a belt holster, or a piece of jewelry. The event time recording device 300 may also include some unrelated device functionality 380, which is not related to the function of user actuation. In some implementations, the event time recording device 300 is actuated during a symptomatic event by an actuation button 310 that is communicably coupled to the event time recording device 300. In other implementations, the device 300 may be actuated by voice command or automatically actuated based on the subject's movements, as described above.

Upon actuation, either by a user pressing the actuation button 310 or by any other means, an actuation switch 320 may close, thus signaling that a symptomatic event has been indicated by the subject. In some implementations, this may cause the controller 330 to query the system clock 340 for the current time, and to store a time stamp indication of the symptomatic event into internal memory 350 for later transmission to another device, such as the base station 110. As described above, the event time recording device 300 may also include more than one actuation button 310, each of which may correspond to a different indication by the subject. In some implementations, actuation of the event time recording device 300 may also cause the transmission of an emergency response signal.

In some implementations, the transmitter 360 can send the stored actuation data wirelessly to an intermediate external device such as a base station 110, which may then transmit the stored actuation data over a network 120 to the remote data center 130. In other implementations, the transmitter 360 may send the actuation data directly to a secure remote data center 130. Communications between the event time recording device 300 and the base station 110 or remote data center 130 may be bidirectional or unidirectional, according to various implementations.

The transmission of the recorded actuation data by the transmitter 360 may be scheduled to occur at a particular time, such as at 3:00 am every morning, or at some other time when the subject is likely to be near the base station 110. In some implementations, the transmitter 360 may make repeated attempts to send the data to ensure reception by the base station 110. For example, the event time recording device 300 may repeatedly transmit the recorded timing data for a period of several nights without regard for an acknowledgment from the base station 110. As an example, this may occur on a fourteen day moving window such that the recorded time stamp data for the past fourteen days is broadcast every night. The moving window may be shorter or longer than fourteen days, according to various implementations. The repeated broadcasts by the event time recording device 300 would ensure that, even if the subject is away from the base station 110 for an extended period of time, such as for a vacation, the recorded time stamp data would eventually be received by the base station 110. In this particular implementation, the base station 110 would likely receive redundant time stamp data since the event time recording device 300 repeatedly broadcasts all of the data recorded in the past number of days, but the base station 110 may be programmed to ignore any such redundant time stamp data. This implementation would require only unidirectional communication from the event time recording device 300 to the base station 110, and may thereby simplify the event time recording device 300 and allow it to be smaller and less burdensome for the subject to carry. In turn, this may lead to increased compliance by the subject.

In other implementations, the transmitter 360 may be configured as a transceiver configured to receive command signals or clock synchronization signals from an external device, such as the base station 110. In the example discussed above, the transceiver 360 may attempt transmission of the recorded actuation data at a particular time of day, and repeat the transmission until the transceiver 360 receives a signal back from the base station 110 that it has received the transmitted actuation data. In another example, the transceiver 360 may periodically attempt transmission of the recorded actuation data, and repeat the transmission until the transceiver 360 receives a signal back from the base station 110 that it has received the transmitted actuation data. In another example, instead of automatically sending the actuation data to the base station 110 at a particular time every day, the event time recording device may be configured to receive interrogation signals from the base station 110, and upon receiving such an interrogation signal, the user actuation data may be sent from the transmitter 360. In another example, the transceiver may receive current clock information from an external source such as the base station 110 or a time-keeping radio station or satellite. In this particular implementation, a clock synchronization module 370 may correct the system clock 340 with the proper time on a periodic basis.

Figure 4:
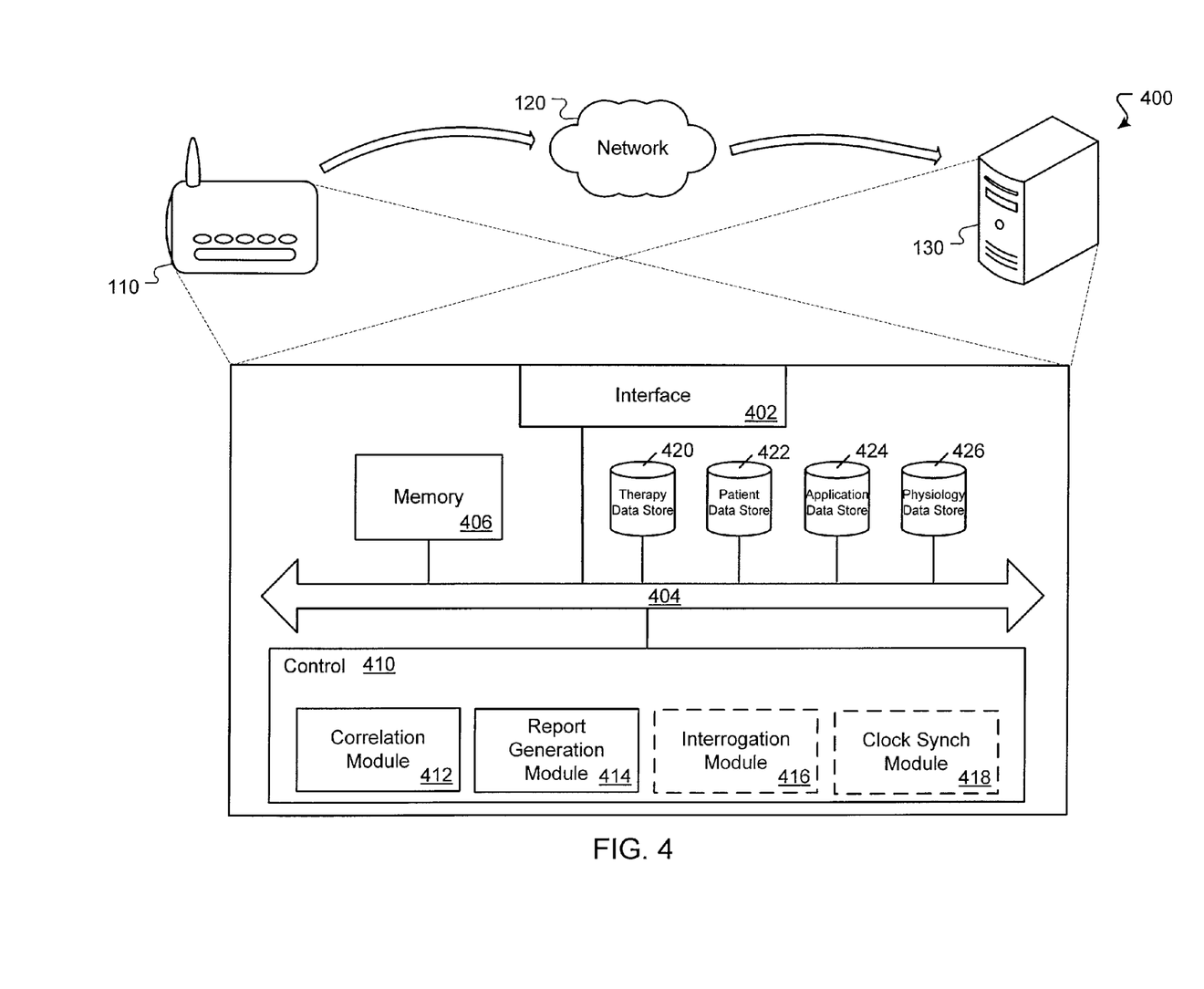
FIG. 4 is a block diagram of a device that correlates sensed biological data with user actuation data.

FIG. 4 is a block diagram of an exemplary system that can be used to receive, analyze, and correlate sensed biological signal data from the subject and user actuation data corresponding to a symptomatic event. In certain implementations, and as shown in FIG. 4, the techniques and procedures disclosed herein can be implemented on either the base station 110 or the remote data center 130, or may be implemented with portions being performed on each. In other implementations, the techniques and procedures may be executed by another type of external computing device such as a handheld computing device (e.g., a PDA, mobile phone, smart phone, etc.) or a personal computer. For simplicity, the discussion with respect to FIG. 4 will focus primarily on the remote data center 130, but it should be known that the block diagram shown in FIG. 4 may also or alternatively exist on the base station 110.

In general, the remote data center 130 is configured to receive the biological signal data from the biological data recording device 102 and the user actuation data from the event time recording device 104, store the data, and correlate the data. In some cases, the remote data center 130 is configured to create a report 140 of the correlated data so that a health care professional can view the sensed biological data that corresponds to a particular symptomatic event.

As shown in FIG. 4, the remote data center 130 includes components or modules that can be used to correlate the biological signal data with user actuation data to allow more efficient analysis of a subject's symptomatic events. Biological signal data and user actuation data may be received by the remote data center 130 through an interface 402. In system implementations including intermediate external devices such as a base station 110, the interface 402 of the remote data center 130 may receive data over a communication channel or over a network 120, for example, from the base station 110. In certain implementations, this data can be sent from the base station 110 to the remote data center 130 over a wired or wireless communication connection, including over a local area network, a wide area network, a cellular communications network, or the Internet, for example. In other implementations, the interface 402 may be configured to receive the biological signal data and user actuation data directly. In implementations where the block diagram of FIG. 4 is part of the base station 110, the interface 402 may receive the sensed signal readings directly from the biological recording device 102 and the event time recording device 104, as is discussed above in connection with FIGS. 2 and 3.

In some implementations, the interface 402 may send the received data along a bus 404, which provides interconnectivity between the various modules and components of the remote data center 130. A control module 410 may include hardware and software modules, including one or more processors (not shown) that may execute instructions to perform tasks for the system, such as steps comprising the methods disclosed herein. Examples of processors that may be suitable can include one or more microcontrollers, central processing units (CPUs), computational cores instantiated within a programmable device or ASIC, and the like. In general, the processor or other control components of the control module 410 may control or manage the flow of information throughout the system, including the flow of information over the bus 404. As is conventional, instructions and data may be stored in a non-volatile data store, and may be moved to a memory 406 for active use. The processor may access the instruction data from memory 406 for execution, for example, and may load the instructions and data into on-chip cache as appropriate.

The remote data center 130 can receive, process, and transmit information regarding the correlation between certain biological signal data and symptomatic events felt by a subject, as indicated by the subject actuating the event time recording device 104. The depicted control module 410 includes a correlation module 412, which can be used to implement the correlation techniques discussed herein. Biological signal data may be presented to a health care professional in the form of a report 140 generated by the remote data center 130. The report 140 may be displayed on a display screen or printed in a hospital, care center, remote data center, or the like. The information in the report 140 may be organized and presented in any number of ways, according to various users' preferences. For these purposes, the control module 410 may include a report generation module, which can be used to generate printed, e-mailed, text messaged, faxed, or displayed reports 140 for analysis by a health care professional or any other end user. In some implementations, the control module 410 can use the correlation module 412 and the report generation module 414 to highlight symptomatic events felt by the patient, to discard or at least not report biological signal data from non-symptomatic events, or to treat the recorded symptomatic events and non-symptomatic events in accordance with a user's preferences.

The control module 410 may optionally include an interrogation module 416, which can be configured to automatically or periodically interrogate the biological data recording device 200 and/or the event time recording device 300 when the devices are in range. As described above, when the devices are configured to receive an interrogation signal, they may respond by sending the sensed biological data or the user actuation data to the interrogating device.

The control module 410 may also optionally include a clock synchronization module 418, which can analyze the incoming sensed biological data and user actuation data and determine whether the timing signals from the two devices are in synch, and if not, apply a correction algorithm to correct for the time drift in either or both of the devices. For example, if the event time recording device 300 is set to broadcast recorded user actuation data at 3:30 am every morning, and the base station 110 receives the transmission at 3:32 am, the clock synchronization module 418 may adjust the received timing data by two minutes to adjust for the inaccurate time on the event time recording device 300. The clock synchronization module 418 may similarly allow for the adjustment of received timing data in the case where the subject changes time zones and forgets to correct the clock on the event time recording device 300. The clock synchronization module may also be configured to send updated time information to one or both of the biological data recording device 200 or the event time recording device 300 in the case that either of those devices include a receiver for receiving such information.

The control module 410 may also request data from various data stores. For example, a therapy data store 420 may store data relating to patient therapies, a patient data store 422 may store subject-specific information, an application data store 424 may store information relating to graphically displaying correlated biological data reports, and a physiology data store 426 may store medical information relating to possible patient states. The control module 410 can process and/or correlate the biological signal data and user actuation data and pass the processed and/or correlated data or information derived from analysis of the data to the interface 402 over the bus 404. From there, the interface 402 may forward the data, for example, to a monitoring device.

Information applied to calculations and analyses performed in the report generation module 414 can include data from various data stores within the remote data center 130. These data stores can store received information from a health care professional. The data stores can also store information received from a subject. The data stores can be updated on a periodic basis. In the depicted implementation, the data stores 420-426 reside within the remote data center 130, but in other implementations, one or more of the data stores 420-426, or other data stores storing other relevant information, may be external to the device, and may be accessed by the device or by another device that provides the information to the remote data center 130.

The therapy data store 420 can store information regarding patient therapy methods, such as a cardiac rhythm management device. For example, this information can provide data to the control module 410 to determine heart rate thresholds or risk indicator thresholds.

Information regarding the subject can also aid in determining which of the biological signals to display and how to display them. The patient data store 422 can include patient information such as drug allergies, previous cardiac history, and current or historical health care providers. The control module 410 can use information from the patient data store 422 to modify an assessment of the subject's overall health condition.

The physiology data store 426 can also provide information to aid in determining which of the biological signals to display and how to display them. The physiology data store 426 can include historic patient vital signs and trends, other risk markers determined with external or implantable devices, and other pre-existing conditions, to list just a few examples. This data can be used with the techniques described herein to provide a more complete biological report to the physician or health care provider, according to some implementations.

Figure 5:
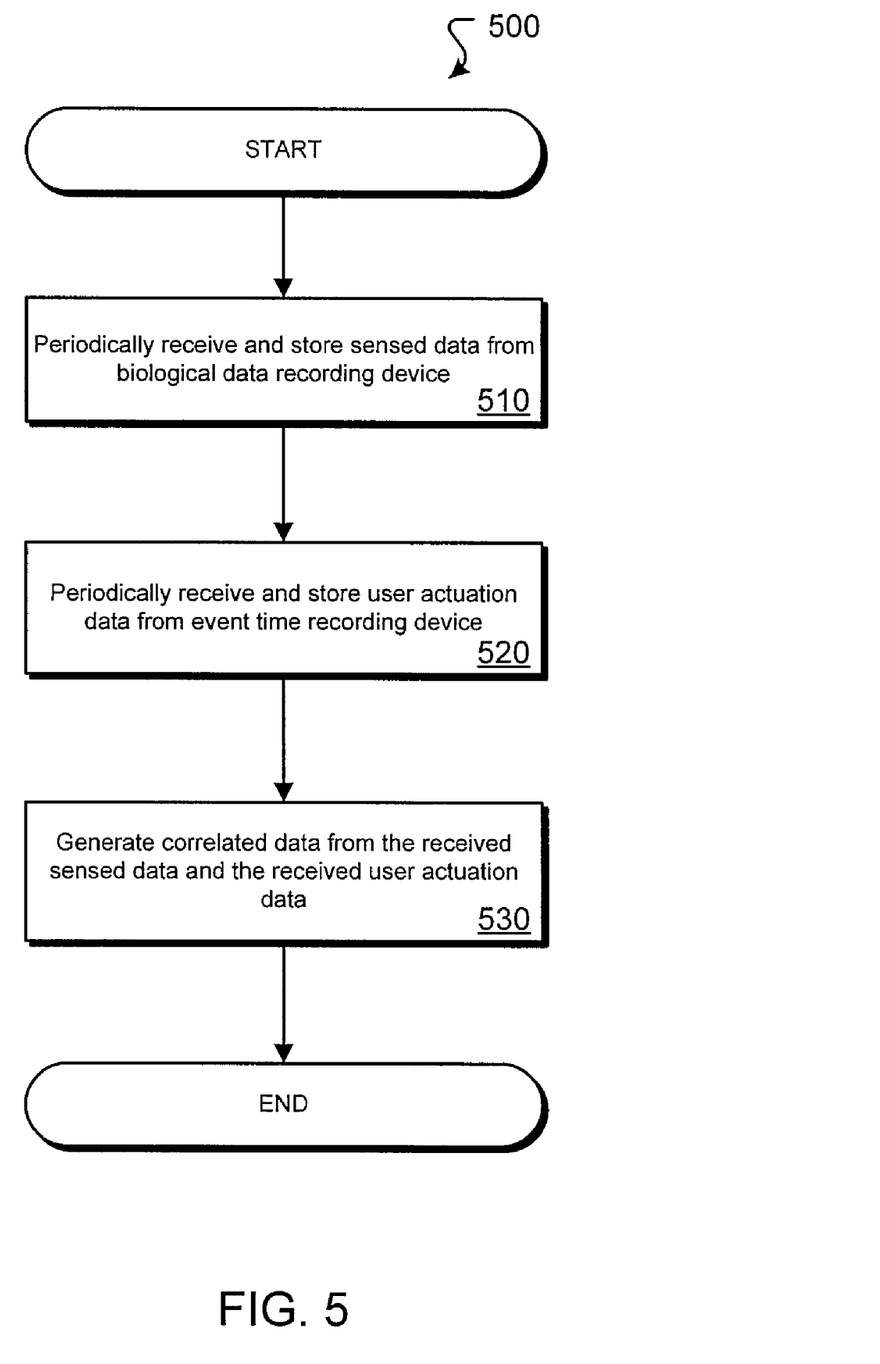
FIG. 5 is a flow chart of an example process for obtaining and correlating sensed biological data with user actuation data.

FIG. 5 is a flow chart 500 of exemplary operations that can be executed to correlate sensed biological data with user actuation data, thus providing, for example, improved analytical processing of the sensed biological data based upon a subject's symptomatic episodes, according to certain implementations.

At an initial step 510, a base station 110 for example, may periodically receive and store sensed data from a biological data recording device. As one example, the base station 110 may continuously wait for incoming transmitted signals from the biological data recording device, and when the device is in range and transmits the data, the base station 110 may receive the data and store it. As another example, the base station 110 may wait for incoming transmitted signals from the biological data recording device only during a certain time window, such as between 2:30 am and 3:30 am. As another example, the base station 110 may be more active in receiving the data by periodically interrogating the biological data recording device, which in turn will transmit the data to the base station 110 when it is in range.

At another step 520, a base station 110 for example, may also periodically receive and store user actuation data from an event time recording device. As one example, the base station 110 may continuously wait for incoming transmitted signals from the event time recording device, and when the device is in range and transmits the data, the base station 110 may receive the data and store it. As another example, the base station 110 may wait for incoming transmitted signals from the event time recording device only during a certain time window, such as between 2:30 am and 3:30 am. As another example, the base station 110 may be more active in receiving the data by periodically interrogating the event time recording device, which in turn will transmit the data to the base station 110 when it is in range. It should be understood that the order of steps 510 and 520 may be performed in any order, or even simultaneously.

Next, at step 530, a base station 110 or a remote data center 130 for example, may generate correlated data from the received sensed biological data and the received user actuation data. This step 530 is described in more detail in connection with FIGS. 6A and 6B.

Figure 6A:
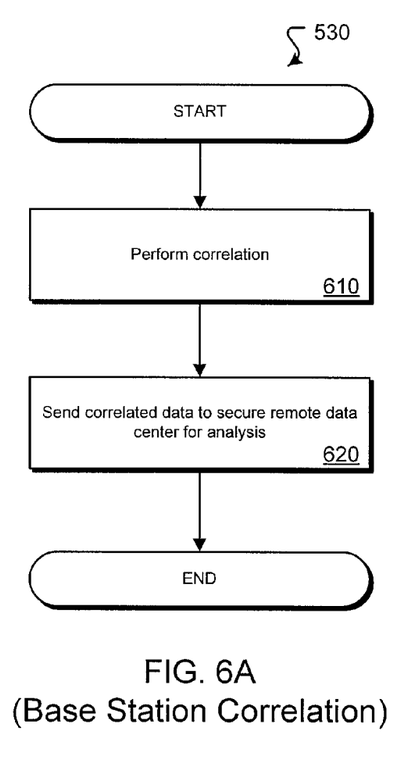
FIGS. 6A-6B are flow charts of alternative example processes for performing portions of the flow chart in FIG. 5.

FIG. 6A shows a flow chart of exemplary operations that can be executed to perform the step 530 on the base station 110 of the system. According to this particular implementation, a significant portion of the analytical processing may be done on the base station 110, thus allowing less data to be sent to a secure remote data center 130 for further processing. In this implementation, the base station 110 has already received the sensed biological data and the user actuation data, as described above at steps 510 and 520.

The next step 610, which may also performed on the base station 110, is the correlation of the sensed biological data and symptomatic events felt by the patient, as indicated by the time stamp information stored as user actuation data. In this step 610, the base station 110 may cycle through each of the instances of user actuation contained in the user actuation data and determine whether any corresponding recorded biological data exists, and if so, correlate the biological signal data with the user actuation data. Whether an instance of user actuation corresponds to a set of biological data, and should therefore be correlated, may be determined by a number of different procedures. As one example, a user actuation event may correspond to a set of biological data only if the user actuation event occurs at or near the same time as the beginning of a biological recording. In another example, a corresponding user actuation event may fall at any point during the course of a biological recording. In another example, the user actuation event may be within a time period after the biological signal data was recorded, which would be useful if the subject was unable to feel any symptoms or actuate the device prior to fainting, but remembered to actuate the device shortly after waking.

The base station 110 may treat any non-correlated biological signal data according to a user's preferences. For example, the non-correlated biological signal data may be either disregarded or otherwise processed differently than the correlated biological signal data. In another example, the biological signal data that was not correlated to a symptomatic event felt by the subject may still be sent along for further analysis and processing, but would remain non-correlated. As shown in FIG. 6A, the next step 620 may be for the base station 110 to then send the correlated data (and possibly the non-correlated data, according to certain implementations) to a secure remote data center for further analysis and processing.

Figure 6B:
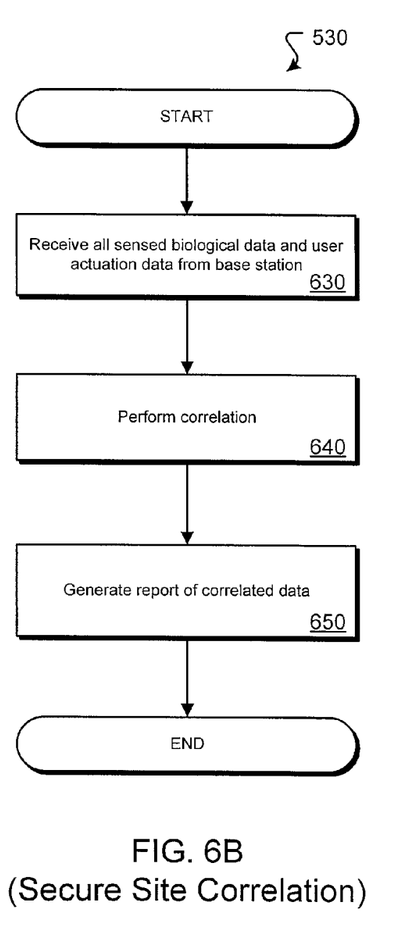

FIG. 6B shows an alternative flow chart of exemplary operations that can be executed to perform the step 530 at the secure remote data center 130 of the system. According to this particular implementation, the base station 110 may act primarily as an intermediate device that receives the sensed biological data from the biological data recording device and the user actuation data from the event time recording device and stores them temporarily before then sending the entire set of data along to the remote data center 130. According to this implementation, certain processing may be done on the data while on the base station 110, but the correlation steps are not done on the base station 110. In some implementations, an intermediate base station 110 may not be included in the system 100.

At step 630, and as depicted in FIG. 6B, the secure remote data center 130 may receive all of the sensed biological data and user actuation data from the base station 110. Alternatively, the remote data center 130 may receive the sensed biological data and user actuation data directly from the respective devices, 200 and 300. Next, the remote data center performs the correlation at step 640, according to various users' preferences. For example, in one implementation, the remote data center 130 may cycle through each of the instances of user actuation contained in the user actuation data and determine whether any corresponding recorded biological data exists, and if so, correlate the biological signal data with the user actuation data. Similar correlation procedures to those discussed above may be used. In some implementations, the data center 130 may then discard any non-correlated biological signal data. In another example, the non-correlated biological signal data may still be stored for further analysis and processing, but would not be correlated to a symptomatic event in the subject.

At step 650, the remote data center 130 may generate a report 140 of the correlated biological data (and possibly non-correlated biological data, in some implementations) for use by a health care professional or other end user. In certain implementations, the end user may be a physician or any other healthcare provider, or may be the subject. In some implementations, the end user may be a computer or program that further processes the report 140.

A number of implementations have been described. Nevertheless, it will be understood that various modifications may be made without departing from the spirit and scope of the systems, methods, and devices described herein. For example, the base station and biological data recording device may use an asynchronous push/pull data transfer mechanism to transfer the data from the recording device to the base station. Similarly, the event time recording device may use an asynchronous push/pull data transfer mechanism to transfer the data from the device to the base station. In addition, wireless, wired, telemetric, Bluetooth, and/or other data transfer protocols may be used to transfer the data from the recording device and/or the event time recording device to the base station. Accordingly, other embodiments are within the scope of the following claims.

What is claimed is:

1. A system for obtaining and analyzing biological data of a user, the system comprising:
    a) a biological data recording device adapted to sense and record, in a first memory, a plurality of biological data events, each biological data event being representative of a biological condition of a user that is sensed by the biological data recording device;
    b) an event time recording device that is incapable of either direct or indirect communication with the biological data recording device, the event time recording device comprising a user actuatable component and a recording component adapted to store, in a second memory, user actuation data consisting of a time stamp indication as to when an instance of user actuation occurred; and
    c) an analysis station that is remote from the biological data and the event time recording devices and adapted to receive, periodically, the stored plurality of biological data events from the biological data recording device and the stored user actuation data from the event time recording device,
    d) wherein the analysis station is adapted to correlate the user actuation data with the plurality of biological data events to thereby generate correlated biological data that is usable to diagnose the root cause of a symptomatic event.

2. The system of claim 1, wherein the biological data recording device is an electrocardiogram (ECG) recording device.

3. The system of claim 2, wherein the biological data recording device is implantable and has a wireless transmitter to transmit recorded biological data from the first memory to a wireless receiver comprising the analysis station.

4. The system of claim 3, wherein the event time recording device has a wireless transmitter to transmit user actuation data from the second memory to a transceiver comprising the analysis station.

5. The system of claim 1, wherein the event time recording device has a wireless transmitter to transmit user actuation data from the second memory to a transceiver comprising the analysis station.

6. The system of claim 1, wherein the event time recording device is a timekeeping device.

7. The system of claim 6, wherein the timekeeping device is a watch.

8. The system of claim 1, wherein the event time recording device is a keychain.

9. The system of claim 1, wherein the analysis station is further adapted to correct timing information in either the biological data or the user actuation data.

10. The system of claim 1, wherein the event time recording device has a transmitter to periodically transmit user actuation data from the second memory to the analysis station.

11. A method for obtaining and analyzing biological data of a user, the method comprising the steps of:
    a) providing an analysis station;
    b) providing a biological data recording device adapted to sense and record a plurality of biological data events, each biological data event being representative of a biological condition of a user that is sensed by the biological data recording device;
    c) providing an event time recording device that is incapable of either direct or indirect communication with the biological data recording device, the event time recording device comprising a user actuatable component and a recording component that records a time stamp indication when the user actuatable component was actuated;
    d) receiving the biological data events and the user actuation data at the analysis station, which is remote from the biological data and the event time recording devices;
    e) correlating the user actuation data with the plurality of biological data events at the analysis station; and
    f) presenting the correlated user actuation data and the biological data in a format that is capable of being analyzed by a health care provider to thereby aid in diagnosis of the root cause of a symptomatic event and subsequent treatment of the user.

12. The method of claim 11 including correlating the user actuation data to user actuation of the event time recording device made upon sensing a cardiac symptom.

13. The method of claim 11 including providing the biological data recording device as an electrocardiogram (ECG) recording device.

14. The method of claim 13 including providing the biological data recording device as being implantable and comprising a wireless transmitter to transmit recorded biological data to the analysis station.

15. The method of claim 14 including providing the event time recording device comprising a transceiver to transmit user actuation data to the analysis station.

16. The method of claim 11 including providing the event time recording device comprising a transceiver to transmit user actuation data to the analysis station.

17. The method of claim 11 including providing the event time recording device as a timekeeping device.

18. The method of claim 17 including providing the timekeeping device as a watch.

19. The method of claim 11 including providing the event time recording device as a keychain.

20. The method of claim 11 including correlating, at the analysis station, a biological data event to a user actuation event meeting at least one of the following criteria:
 a) user actuation data that occurs at or near the beginning of a biological data event;
 b) user actuation data that falls at any point during the course of a biological data event; and
 c) user actuation data that is within a defined time period after the biological data event was recorded.

* * * * *